United States Patent [19]

Rhodes et al.

[11] Patent Number: 5,541,171
[45] Date of Patent: *Jul. 30, 1996

[54] ORALLY ADMINISTRABLE PHARMACEUTICAL COMPOSITION

[75] Inventors: John Rhodes, Cardiff; Brian K. Evans, Dinas Powis, both of Wales

[73] Assignee: Tillotts Pharma AG, Ziefen, Switzerland

[*] Notice: The term of this patent shall not extend beyond the expiration date of Pat. No. 5,541,171.

[21] Appl. No.: 448,300

[22] Filed: May 23, 1995

Related U.S. Application Data

[63] Continuation of Ser. No. 32,167, Mar. 12, 1993, which is a continuation of Ser. No. 858,449, Mar. 20, 1992, which is a continuation of Ser. No. 584,386, Sep. 14, 1990, which is a continuation of Ser. No. 735,727, May 20, 1985, which is a continuation of Ser. No. 482,331, Mar. 30, 1983 which is a continuation of PCT/GB82/00235, Jul. 28, 1982.

[30] Foreign Application Priority Data

Jul. 31, 1981 [GB] United Kingdom ................ 8123573

[51] Int. Cl.⁶ .................. A61K 31/615; A61K 31/60; A61K 9/28
[52] U.S. Cl. .................. 514/166; 424/457; 424/474; 424/489; 424/490; 514/159
[58] Field of Search ................ 514/166; 424/81

[56] References Cited

U.S. PATENT DOCUMENTS

| | | | |
|---|---|---|---|
| 3,775,537 | 11/1973 | Lehmann et al. | 424/21 |
| 3,784,683 | 1/1974 | Prillig et al. | 424/469 |
| 3,935,326 | 1/1976 | Groppenbacher et al. | 424/32 |
| 3,954,959 | 5/1976 | Pedersen | 424/21 |
| 4,060,598 | 11/1977 | Groppenbacher et al. | 424/33 |
| 4,083,949 | 4/1978 | Benedikt | 424/19 |
| 4,190,716 | 2/1980 | Parkinson | 424/78 |
| 4,496,553 | 1/1985 | Halskov | 514/166 |
| 4,980,173 | 12/1990 | Halskov | 514/81 |

FOREIGN PATENT DOCUMENTS

| | | | |
|---|---|---|---|
| 40590A | 6/1981 | European Pat. Off. | 514/81 |
| 1017674 | 1/1966 | United Kingdom . | |
| 1219026 | 1/1971 | United Kingdom . | |
| 2021409 | 1/1979 | United Kingdom | 514/81 |
| 8102671 | 9/1981 | WIPO | 514/81 |

OTHER PUBLICATIONS

Goodman et al., *Ulcerative Colitis*, pp. 111 and 121 (1978).
Khan et al., "An Experiment . . . Sulphasalazine", *Lancet* 2, pp. 892–895 (1977).
Röhm Pharma, "Eudragit L and S Appli. in the Production of Pharm. Preps.", pp. 2–7, (1973).
Lehmann, "Acrylic Coatings . . . Manuf.", *Manufacturing Chemist*, pp. 39–41 (1973).
Röhm Pharma, "Eudragit Lacquers for Tablet Coating", pp. 9–29 and 30 (1973).
Dew et al., *Brit. Med. J.*, vol. 285, pp. 1012 (1982).
Stolk, L. M. L., et al., Pharmaceutisch Weekblad Scientific Edition, 12(5), 200–204 (1990).
Rijk, M. C. M., et al., Scand J. Gastroenterol, 27, 863–868 (1992).
"An Oral Preparation to Release Drugs in the Human Colon" *Br. J. Clin. Pharmac.* (1982), 14, 405–408, M. J. Dew et al.
"Colonic Release of 5-Amino Salicylic Acid From an Oral Preparation in Active Ulcerative Colotis" *Br. J. Clin. Pharmac.*, 16, 185–187, M. J. Dew et al (1981).
"Comparison of the Absorption and Metabolism of Sulphasalazine and Acrylic–coated 5–Amino Salicylic Acid in Normal Subjects and Patients with Colitis", *Br. J. Clin. Pharmac.* (1984), 17.000–000, M. J. Dew et al.

*Primary Examiner*—Shelley A. Dodson

[57] ABSTRACT

A solid dosage form, such as a capsule or tablet, containing a pharmacologically active agent is coated with an anionic polymer, which is insoluble in gastric juice and in intestinal juice below pH7 but soluble in colonic intestinal juice, in a sufficient amount that the oral dosage form remains intact until it reaches the colon. The preferred anionic polymer is a partly methyl esterified methacrylic acid polymer in which the ratio of free carboxylic groups to ester groups is about 1:2. The invention has particular application to dosage forms of prednisolone and salts thereof, indomethacin, ibuprofen, and, especially, 5-amino-salicylic acid.

19 Claims, No Drawings

ORALLY ADMINISTRABLE PHARMACEUTICAL COMPOSITION

This application is a continuation of application Ser. No. 08/032,167 filed Mar. 12, 1993 which is a continuation of 07/858,449 filed Mar. 20, 1992 which is a continuation of 07/584,386 filed Sep. 14, 1990 which is a continuation of 06/735,727 filed May 20, 1985 which is a continuation of 06/482,331 filed Mar. 30, 1983, which is a continuation of PCT/GB82/00235, filed Jul. 28, 1982.

The present invention relates to the administration of pharmacologically active agents to the large intestine and provides an orally administrable pharmaceutical composition for said purpose. It has particular, but not exclusive, application to the administration of 5-amino-salicylic acid (hereinafter referred to as 5-ASA) for the treatment of colonic or rectal disorders.

In the treatment of diseases or ailments of the colon or rectum administration of the pharmacologically active agent to the affected site may be required. Orally administrable pharmaceutical compositions however have frequently been found ineffective in this respect as a result of the absorption of the pharmacologically active agent in the digestive tract before the colon or rectum is reached. Consequently, the delivery of pharmacologically active agents to the colon or rectum has conventionally been achieved by rectal administration, by the use of either suppositories or enemas. However, rectal administration generally is less convenient and less acceptable to a patient than oral administration. Further, said rectal administration is not suitable for treating the right side of the colon. In particular, suppositories are only effective for the rectum and enemas rarely reach beyond the left side of the colon.

Several "delayed release" forms of orally administrable pharmaceuticals have been proposed. The delayed release may result from the physical properties of the pharmaceutical composition or from the chemical and physical properties of a derivative of the active ingredient. It is known to provide tablets and capsules for oral administration with a coating which will disintegrate to release the pharmacologically active agent gradually when the tablet or capsule has reached the acid environment of the stomach or the alkaline environment of the small intestine. Similarly it is known to provide tablets and capsules with a coating permeable to the pharmacologically active agent contained within and through which the agent is gradually released.

It has been proposed in UK Patent Specification No. 1219026 (published January 1971) to embed individual particles of a pharmacologically active agent in a slowly disintegrating or slowly dissolving resin having a particular dissolution profile to provide an orally administrable pharmaceutical composition for selectively administering the agent to the large intestine. The resin is selected such that the agent remains substantially protected by the resin while the particles travel through the stomach and small intestines of a patient and that the agent is substantially completely exposed at the time the particles reach the large intestine. In particular, the nature and amount of the resin is selected so that when a quantity of the embedded agent is introduced into a Stoll-Gershberg disintegration apparatus, submerged in a simulated intestinal fluid (made in accordance with the U.S. Pharmacopoeia, Volume XVII, 1965 at page 919 but modified by containing no pancreatin), and operated as described in the patent specification, 2% to 12% of the agent dissolves within an hour of the introduction of the agent into the fluid and 18% to 88% of the agent dissolves within three hours of said introduction. It is specifically stated that the resin is selected so that the dissolution rate of the agent is not pH dependent but is time dependent. The preferred resin is a high-viscosity grade modified vinyl acetate resin (available under the Registered Trade Mark "Gelva" C3-V30) and other specified resins are carboxylated polyvinyl acetates, polyvinyl/maleic anhydride copolymers, poly(methacrylic acid), ethylene/maleic anhydride copolymers, ethyl cellulose, methylacrylic acid/methyl methacrylate copolymers, waxes and mixtures thereof including mixtures with shellac. Tablets of the embedded particles coated with a standard coating solution containing cellulose-acetate-phthalate are reported.

It will be appreciated that the carrier system disclosed in UK Patent Specification No. 1219026 relies upon the rate of disintegration or dissolution of the resin as the preparation passes through the gastrointestinal tract. This time dependency makes it impossible to limit administration of the agent to the colon because of large variations in the transit time in the gastro-intestinal tract, especially in the stomach, which occur between different patients and in the same patient from time to time. It would appear that the carrier system has not been satisfactory in practice because we are not aware of any relevant product presently available in the UK or elsewhere and further we understand that the patent lapsed in 1979 by non-payment of renewal fees.

Anionic polymers have been known for many years to be of use in the preparation of coatings for tablets and other oral dosage forms to provide delayed or sustained release of the active agent. In particular, it has been known since at least 1974 to use for said coatings anionic copolymers of methyacrylic acid and methacrylic acid methyl ester. Such a copolymer (available under the Registered Trade Mark "Eudragit" S) in which the ratio of free carboxyl groups to ester groups is approximately 1:2 and having a mean molecular weight of 135,000 is known to be insoluble in gastric juice and poorly soluble in intestinal juice while an analogous copolymer (available under the Registered Trade Mark "Eudragit" L) differing only in so far as said ratio is approximately 1:1 also is insoluble in gastric-juice but is readily soluble in intestinal juice. Said copolymers are usually employed to provide a coating of between about 25 and about 40 microns thick and the poorly soluble (in intestinal juice) copolymer usually is employed to reduce the dissolution (in intestinal juice) of the readily soluble copolymer. In general terms, anionic polymer coatings-on oral dosage forms have been required to dissolve in aqueous medium at a pH below 7, usually between pH 5.5 and pH 7. Eudragit S dissolves above pH 7 but, as noted above, usually is employed in admixture with Eudragit L. As far as we are aware, said mixtures invariably dissolve below pH 7.

Salicylazosulphapyridine (also known as sulphasalazine or salazopyrin and hereinafter referred to as SASP) consists of sulphapyridine linked to a salicylate group by a diazo bond and has been found to be useful in the treatment of colitis, Crohn's disease, idiopathic proctitis and chronic arthritis. Orally administered SASP is only absorbed to a limited extent before reaching the colon where azo-reductases produced by colonic bacteria act to split SASP into sulphapyridine and 5-amino-salicylic acid (i.e. 5-ASA). Studies by A.K.A. Khan et al. (The Lancet, Oct. 29 1977, p. 892) and others have shown the 5-ASA to be the pharmacologically active agent in the treatment of colonic and rectal ailments with SASP. Sulphasalezine appears merely to act as a chemical carrier to deliver 5-ASA to the colon and rectum. When administered orally without the azo-bond joining them, sulphapyridine and 5-ASA are almost entirely absorbed from the small intestine before reaching the colon.

Several proposals have been made for the oral administration of 5-ASA avoiding using SASP in order to reduce the occurrence of side effects attributable to the sulphapyridine moiety. For example, in U.S. Pat. No. 4,190,716 (published February 1980), it was proposed to covalently bond the 5-ASA to a nonabsorbable pharmacologically acceptable organic polymer backbone comprising a plurality of aromatic rings by azo bonds bridging aromatic carbon atoms and the 5-position carbon of 5-ASA.

In UK Patent Specification No. 2021409 (published December 1979), it was proposed that 5-ASA should be administered concurrently or concomitantly with certain disodium cromoglycate-like compounds. Reference is made to formulating 5-ASA in sustained or controlled release form by coating some or all 5-ASA particles or granules thereof with a slowly soluble or digestable or semipermeable layer of material such as beeswax, Carnuba wax, stearic or palmitic acids or cetyl alcohol. Reference also is made to coating tablets of the coated or uncoated 5-ASA with a continuous film of a material such as shellac or cellulose acetate phthalate which is resistant and impermeable to gastric secretions but susceptible to intestinal secretions. None of the coating materials specified or indicated in the specification are such as to prevent release of 5-ASA until the colon.

More recent proposals have been made in International Patent Specification No. WD 81/02671 (published 1st Oct. 1981) and European Patent Specification No. 40590A (published 25 Nov. 1981), both of which specifications were published after the priority date of the present application. The International Specification proposes formulating 5-ASA in a sustained release tablet or enterosoluble tablet form and specifies ethyl cellulose as the preferred coating material. No coating materials other than cellulose derivatives are mentioned and it is granules, as distinct from tablets or other solid oral dosage forms, which are described as being coated.

The European Specification proposes coating a core of 5-ASA with a coating material comprising at least, (a) 10 to 85% by weight of an anionic carboxylic polymer soluble only above pH 5.5 and (b) 15 to 90% by weight of a water-soluble, quaternary ammonium substituted acrylic polymer. It is stated that the coating normally will be 3 to 60, preferably 10 to 30, microns thick and that partly methyl esterified methacrylic acid polymers are suitable anionic carboxylic polymers for use as component (a). In the Examples, Eudragit L and a mixture of Eudrogit L and Eudragit S constitute the component (a) and in all cases the coatings dissolved at below pH 7. The coated bodies of the European Application are subsequently included in dosage units which normally contain at least 10 coated bodies. The rationale of the coating system is stated to be that the change of pH from acid to neutral at the pylorus triggers a change in the physical condition of the coating so that 5-ASA is subsequently released after a predetermined time lag by which time the preparation should have reached the colon. Although time of passage through the small intestine is relatively constant, it still varies from 2 to 5 hours and hence the carrier system does not provide for reliable release of 5-ASA only in the colon. Eudragit L and Eudragit S are products of Rhom Pharma GmbH, 6100 Darmstadt, Federal Republic of Germany.

The Inventors have now found that 5-ASA reliably can be administered specifically to the large intestine, especially the colon, by simply coating a solid oral dosage form with a sufficient thickness of a partly methyl esterified methyacrylic acid polymer which does not dissolve in aqueous medium below pH 7 but does dissolve below pH 7.5. This carrier system differs from those previously disclosed in relation to 5-ASA in that dissolution or disintegration does not occur until entry of the coated dosage form into the colon. In particular, there is substantially no leaching out of the 5-ASA downstream of the colon in the normal patient. Further, the system involves coating of the solid oral dosage form itself and not necessarily the coating of individual particles contained therein and hence the coated dosage form is relatively inexpensive and easy to manufacture. It is believed that the carrier system is entirely new in concept and of application to a wide range of pharmacologically active agents and anionic polymers.

According to a first aspect of the present invention, there is provided an orally administrable pharmaceutical composition for selectively administering a pharmacologically active agent to the large intestine comprising a solid oral dosage form containing said agent and coated with an anionic polymer which is insoluble in gastric juice and in intestinal juice below pH 7 but soluble in colonic intestinal juice, for example below pH 7.5, said coating being sufficiently thick that the oral dosage form remains intact until it reaches the colon.

According to a second aspect of the present invention, there is provided a process of preparing an orally administrable pharmaceutical composition for selectively administering a pharmacologically active agent to the large intestine which comprises coating a solid oral dosage form containing said agent with an anionic polymer, which is insoluble in gastric juice and in intestinal juice below pH 7 but soluble in colonic intestinal juice, in a sufficient amount that the oral dosage form remains intact until it reaches the colon.

According to a third aspect of the present invention, there is provided a method of treating colonic and rectal disorders which comprises administering to a patient suffering such disorder a coated oral dosage form of the invention.

It is expected that any anionic polymer having the dissolution profile specified above can be used in the practice of the invention subject, of course, to compatibility with the relevant active agent. However, presently preferred polymers are anionic carboxylic polymers i.e. polymers in which the anionic groups are at least predominantly free carboxylic and/or esterified carboxylic groups. It is particularly preferred that the polymers should be acrylic polymers and the presently most preferred polymers are partly methyl esterified methacrylic acid polymers in which the ratio of free carboxylic groups to ester groups is about 1:2 (i.e. Eudragit S). Eudragit S is a lacquer for coating tablets or other solid pharmaceutical preparations to make them impervious to water, resistant to gastric juice yet soluble in the neutral or slightly alkaline intestinal medium. Eudragit S is an anionic polymer synthesized from methacrylic acid and methacrylic acid esters, has the formula:

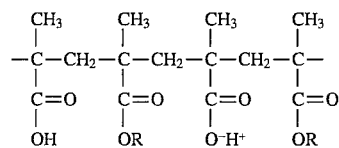

and is supplied by Röhm Pharma, GMBH, Darmstadt, Germany. As previously stated, the anionic polymer should be insoluble in gastric juice and intestinal juice having a pH below 7. However, the polymer must dissolve in colonic intestinal juice, especially below pH 7.5, in order to make the active agent available in the large intestine, especially the colon.

The coating can, and usually will, contain a plasticiser and possibly other coating additives such as coloring agents, gloss producers, talc and/or magnesium stearate as well known in the coating art. In particular, anionic carboxylic acrylic polymers usually will contain 10 to 25% by weight of a plasticiser especially diethyl phthalate. Conventional coating techniques such as spray or pan coating are employed to apply the coating. (See for example D. Dreher "Film coatings on acrylic resin basis for dosage forms with controlled drug release" Pharma International 1/2 (1975) 3). As previously mentioned, the coating thickness must be sufficient to ensure that the oral dosage form remains intact until the colon is reached. It has been found that a coating of between 60 and 150 microns usually is required. Preferably, the coating is between 75 and 125 microns, especially between 80 and 100 microns. Obviously, a certain amount of trial-and-error experimentation will be required before ascertaining the optimum thickness of a particular polymer on a particular solid oral dosage form but such experimentation is well within the capability of a man of average skill in the art.

The term "solid oral dosage form" means any non-liquid dosage form intended to be swallowed and having a sufficiently defined form to be coated. Usually, the dosage form will be a conventional tablet or a capsule, e.g. a hard or soft gelatin capsule.

In addition to the pharmacologically active ingredient the oral dosage form may also contain one or more usual additives such as fillers (e.g. lactose or dicalon phosphate), binders (e.g. starch or polyvinylpyrrolidone), lubricants (e.g. magnesium stearate, stearic acid or talc) and disintegrants (e.g. alginic acid, sodium starch glycolate or potato starch). The oral dosage forms may be prepared in conventional manner.

As active agents in the composition of the invention those compounds conventionally used in the treatment of colitis, ulcerative colitis, Crohn's disease, idiopathic protitis and other diseases or disorders of the colon or rectum are of particular interest. Examples of active ingredients include 5-ASA; non-steroidal anti-inflammatory compounds, e.g. salicylates, indomethacin or ibuprofen; steriods, e.g. hydrocortisone, prednisolone, prednisolone phosphate, prednisolone metasulpho-benzoate sodium, prednisolone sodium phosphate, beclomethasone dipropionate and beclomethasone valerate; compounds active in the relief of constipation or diarrhoea, compounds active in the relief of spasm and in the improvement of motility, e.g. peppermint oil and other carminative essential oils; compounds for removal of excessive bile acids, e.g. cholestyramine; antibacterial or antiparasitic compounds, e.g. erythromycin, chloroguine, iodochlorhydroxyquin, disodohydroxyquin, neomycin and tetracyclines.

The invention has particular application to the administration of pregnisolone or a salt thereof, indomethacin, ibuprofen and, especially, 5-ASA to the colon. In more general terms, the carrier system of the invention is particularly useful for the administration of active agents, especially topically active agents, to the right side of the colon which, as mentioned previously, cannot reliably be reached with a rectally administered dosage form.

The pharmacologically active agents will be present in the oral dosage forms in suitable unit dosage amounts. Said amounts will be known or readily ascertainable by those skilled in the art. In many cases, said amounts are likely to be less than those presently administered by conventional delayed or sustained release dosage forms because of the high organ specificity of the dosage form of the present invention.

The following non-limiting Examples are provided to illustrate the compositions of the invention:

EXAMPLE I

A coating composition was prepared in the form of a lacquer containing the following ingredients:

| | | |
|---|---|---|
| EUDRAGIT S100 | | 3 g |
| Diethyl phthalate | | 0.75 ml |
| Silicone fluid DC 200/20CS | | 0.75 ml |
| Methanol | 25 parts } ad | 100 ml |
| Dichloromethane | 75 parts | |

A coating of 12 mg/cm² dried lacquer substance (i.e. about 100 microns) was applied by spraying the above composition onto size No. 1 hard gelatin capsules (Lok-Cap, Eli Lilly) each containing:

| | |
|---|---|
| 5-ASA | 400 mg |
| Lactose | 46 mg |
| Polyrinylpyrolidone | 20 mg |
| Magnesium stearate | 4 mg |
| Alginic acid | 10 mg |
| Total | 480 mg |

EXAMPLE II

The coating composition of Example I was applied to commercially available enterically coated tablets containing 5 mg prednisolone (Deltacortril Enteric Pfizer) to produce a coating of 12 mg/cm² dried lacquer substance (i.e. about 100 microns).

EXAMPLE III

The coating composition of Example I was applied to size No. 1 hard gelatin capsules (Lok-Cap, Eli Lilly) containing:

| | |
|---|---|
| Indomethacin (active agent) | 10 mg |
| Barium sulphate (radiopaque) | 300 mg |
| Potato starch (disintegrant) | 80 mg |
| Lactose (filler) | 50 mg | to produce a coating.

The presence of barium sulphate was required in order to follow the progress of the capules by radiographic techniques.

EXAMPLE IV

Six convalescent patients, 3 male and 3 female with a mean age of 57 years, from a general medical ward gave informed consent to a clinical trial. After breakfast they each swallowed six specially prepared capsules (No. 0 Lok-Cap Eli Lilly) coated with an acrylic based resin (Eudragit-S from Rohm Pharma GMBH) 120 microns in thickness applied by a modified air suspension technique (as described by Ekburg and Kallstand, Svenk.Farm.Tidskr 1972; 74; 375–78). The thickness of the coat was checked using a micrometer to establish the range of thickness and to measure both the wide and narrow end of the capsule. Each capsule contained barium sulphate (300 mg) potato starch (20 mg) and sulphapyridine (300 mg) as a convenient marker Plain abdominal X-rays were taken at 5, 8 and 12 hours after ingestion and blood samples at 0, 3, 5, 7, 9, 12 and 24 hours after ingestion to assay sulphapyridine levels.

Sulphapyridine was analysed by high pressure liquid chromatography (HPLC) using a modification of the method described by Shaw et al (J. Pharm. Pharmacol. 1980;32;67). The analysis was performed on a LiChrosorb 10 RP 18 bonded silica reversed phase column (Merck). The mobile phase was acetonitrile—0.05M potassium dihydrogen phosphate solution (20:80) containing 0.1 per cent tetrabutyl ammonium hydroxide. Sulphapyridine was detected spectrometrically at 260 nm. Serum samples were treated with an equal volume of ethanol to precipitate plasma proteins and after centrifugation, the supernatant was injected on to the chromatograph. Sulphapyridine concentration was read directly from a calibration curve which was linear over the range 1–25 µg/ml (R=0.99).

X-rays showed that capsules remained intact in the stomach and proximal small bowel. In a few patients occasional capsules broke in the distal ileum (4 of 36) but after 12 hours 32 capsules had reached the colon and of these, 23 had broken at this site. Serum levels of sulphapyridine showed a close correlation with radiographic findings. No drug was detected in any patient 3 hours after ingestion of the capsules and in only 2 patients 5 hours after ingestion. Subsequent samples showed rising levels of sulphapyridine which corresponded with the radiological breakdown of capsules. Maximal levels were obtained at 12 or 24 hours after ingestion; the mean level at 12 hours was 8.3 µg/ml and at 24 hours with 10.9 µg/ml.

The results show that with an acrylic based coating of Eudragit-S, 120 microns in thickness, capsules remained intact after oral ingestion until they reached the right side of the colon when the capsule broke releasing its contents. The radiological evidence was particularly helpful since in most instances one could identify the position of capsules within the intestine from soft tissue outlines. The complementary evidence from serum levels of sulphapyridine simply confirms the release and absorption of this marker corresponding with the radiological findings. Sulphapyridine is a useful marker because it is slowly cleared from the serum and one can demonstrate a rising level with progressive absorption from the colon. 5-ASA was not used as a marker because it is relatively poorly absorbed and excreted rapidly after acetylation so that serum levels are very low.

EXAMPLE V

Seventy-two patients who were in remission with ulcerative colitis or proctitis and taking at least 4 sulphasalazine tablets each day gave their informed consent to a clinical trial. Remission was defined as the passage of three or fewer stools each day without blood or slime during the previous month. Thirty-six patients were male and 36 female. Sigmoidoscopy with rectal biopsy was performed initially and patients only entered the trial if the mucosa was normal (grade 1) or oedematous (grade 2). Biopsies were coded and reviewed by a pathologist who graded them as 1 (normal) or grades 2, 3 or 4 representing mild, moderate or severe inflammatory change.

Patients completed diary cards throughout 16 weeks and were asked to note any side effects; they were seen after 4, 12 and 16 weeks. On completion of the trial a further sigmoidoscopy was performed to ensure the muscosa appeared normal. Patients were seen promptly if symptoms recurred and a sigmoidoscopy was performed at that time. A relapse was defined as a recurrence of symptoms with increased stool frequency and blood loss with sigmoidoscopic changes of contact or spontaneous mucosal haemorrhage (grade 3) or the presence of pus with bleeding and ulceration (grade 4).

Blood was taken for a routine blood count and examination of the film at each clinic attendance and measurements of the serum electrolytes and liver function tests were performed initially and after 16 weeks.

The study, which was randomised and double-blind in design, involved using identical placebo tablets for both sulphasalazine and 5-ASA; each patient was given two sets of tablets with either active 5-ASA and placebo sulphasalazine or placebo 5-ASA and active sulphasalazine. The patient's usual dose of sulphasalazine was continued with a minimum dose of 2 grams daily. The tablets of 5-ASA contained 400 mg (ie the amount of 5-ASA contained in 1 gram of sulphasalazine). At least 3 tablets of 5-ASA were taken daily (1200 mg) with an increased dose of 1 tablet for each gram of sulphasalazine above the minimum entry dose of 2 grams for patients taking a high dose of sulphasalazine. Compliance was checked at each hospital visit by counting the number of tablets returned. 5-ASA powder was obtained from Aldrich Chemicals and the tablets were coated by Rohm Pharma GHB using the modified method of Eckberg and Kallstrand 1972 (supra) with an acrylic-based resin (Eudragit-S) with a thickness between 100–130 microns.

Five of the 72 patients were withdrawn from the study; 4 female and 1 male because of pregnancy in 2 females and constipation in a third. A further 2 patients failed to take the medicine regularly. Of the remaining 67 patients, 15 relapsed and 52 completed the trial. Details of the two groups are in Table 1. Nine patients relapsed on 5-ASA and 6 on sulphasalazine; this difference is not statistically significant (chi squared).

Sixteen patients reported side effects of headache, nausea or indigestion on two or more monthly diary cards during the trial period but there was no difference between the 5-ASA and sulphasalazine group. There was no significant changes identified in either the haematological or biochemical parameters which were measured.

Satisfactory biopsies from 61 patients confirmed the absence of inflammation in most patients (51 of 61 patients). Four showed grade 2 inflammation and 6 grade 3. Three patients did not have a biopsy and in 3 others it proved unsatisfactory.

This double-blind study shows that 5-ASA tablets (400 mg) coated with an acrylic-based resin (Eudragit-S) which was between 100 and 130 microns in thickness is as effective as sulphasalazine in maintaining remission in colitis. The trial which involved 72 patients followed relapses over 16 weeks and since previous studies have shown the majority of relapses occur within the first 12 weeks we feel that the design is adequate to demonstrate whether the alternative preparation is as effective as sulphasalazine during this period.

This preparation represents an important advance in the management of patients with colitis since it may be given to those patients who are unable to take sulphasalazine because of allergic or other adverse reactions. Male infertility is also likely to be due to the sulphapyridine component. Greater doses of 5-ASA can be given because of its low toxicity and these may prove to be more effective therapeutically.

TABLE 1

Details of 67 patients treated with 5-amino salicylic acid or sulphasalazine during 16-week trial.

|  | 5-ASA | SLP |
|---|---|---|
| PATIENTS | | |
| Number | 34 | 33 |
| Sex M/F | 14   20 | 21   12 |
| Age ± SD | 44.9 ± 15.3 | 50.2 ± 15.6 |
| Duration of disease ± SD | 7.2 ± 5.5 | 9.3 ± 6.4 |
| Time since last attack | 1.6 ± 1.4 | 2.1 ± 2.3 |
| Extent of Disease: | | |
| Proctitis | 17 | 19 |
| Left sided | 13 | 5 |
| Extensive | 4 | 9 |
| Relapses | 9 | 6 |
| | (p = NS) | |

EXAMPLE VI

Tablets were manufactured to the following formula:

| Placebo | | Active | |
|---|---|---|---|
| Emcompress | 714 mg | 5-ASA | 400 mg |
| Mag. Stearate | 8 mg | Barium Sulphate | 25 mg |
| Barium Sulphate | 25 mg | Lactose | 125 mg |
| Burnt Umber | 6.1 mg | Polyvinylpyrolidone | 6 mg |
| Explotab | 19 mg | Magnesium Stearate | 11.8 mg |
| | 727 mg | Talc | 11.5 mg |
| | | Explotab | 15.7 mg |
| | | | 595 mg |

Matching active and placebo tablets were formulated and produced.

The tablets were coated with the coating solution of Example 1 to provide a thickness of about 120 microns. The rotational speed of the tablets in the coating apparatus was reduced to a minimum in order to reduce the shear. The coating solution during the initial stage was sprayed on to the tablets at as high a rate as possible. Coated active and placebo tablets were examined as follows:

Placebo (a) Disintegration completed in 6 hrs. 20 minutes.
(b) pH of buffer before commencing=7.21
(c) pH of buffer after test=7.16

Active (a) Disintegration incomplete after 6hrs. 36 minutes.
(b) pH of buffer before commencing=7.16
(c) pH of buffer after test=6.549

Control

Buffer solution at pH=7.21. The pH of the buffer solution was checked as follows:

| Time | pH |
|---|---|
| 0 | 7.21 |
| 15 mins. | 7.197 |
| 30 mins. | 7.189 |
| 1 hr. | 7.189 |
| 2 hrs. | 7.185 |
| 3 hrs. | 7.182 |
| 5 hrs. 44 mins. | 7.181 |
| 24 hrs. | 7.195 |

Radiological examination of the coated tablets in patients indicated that their degree of radio-opacity was lower than expected. This could cause problems when a tablet becomes superimposed over another radio-opaque area and therefore it was decided to drill out the centre of one hundred tablets, fill the cavity with $BaSO_4$ powder and re-seal with Eudragit-S coating.

Studies in patients showed that the tablets were easily visible and disintegration commenced in the ascending colon.

We claim:

1. A non-sustained release orally administrable pharmaceutical composition for selectively administering 5-amino-salicylic acid or a pharmaceutically acceptable salt or ester thereof to the large intestine, the composition comprising a solid oral dosage form containing a pharmaceutically effective amount for the treatment of ulcerative colitis or Crohn's disease of said 5-amino-salicylic acid, ester or salt and said oral dosage form is coated with a 60 to 150 micron thick layer of an anionic copolymer of methacrylic acid and methacrylic acid methyl ester in which the ratio of free carboxyl groups to ester groups is about 1:2 and which is insoluble in gastric juice and in intestinal juice below pH 7 but soluble in colonic intestinal juice, whereby the oral dosage form remains intact until it reaches the colon and releases the 5-amino-salicylic acid to the right side of the colon.

2. A composition as claimed in claim 1 wherein the layer is 75 to 125 microns thick.

3. A composition as claimed in claim 2 wherein the layer is 80 to 100 microns thick.

4. A composition as claimed in claim 3 wherein the layer is 80 to 125 microns thick.

5. A composition as claimed in claim 1 wherein the layer is 80 to 125 microns thick.

6. A composition as claimed in claim 1 wherein the solid oral dosage form is a capsule or tablet.

7. A method of treating ulcerative colitis or Crohn's disease comprising orally administering to a person suffering therefrom a composition as claimed in claim 1.

8. A method as claimed in claim 7 wherein the layer is 80 to 125 microns thick.

9. An orally administrable pharmaceutical composition for selectively administering 5-amino-salicylic acid, or pharmaceutically acceptable salt or ester thereof, to the large intestine, comprising a solid oral dosage form containing a pharmaceutically effective amount for the treatment of ulcerative colitis or Crohn's disease of the colon of said 5-amino-salicylic acid, salt or ester, said solid oral dosage form, but not individual particles contained therein, being coated with a layer of composition containing an anionic copolymer of methacrylic acid and methacrylic acid methyl ester, in which the ratio of free carboxyl groups to ester groups is about 1:2, and which layer is insoluble in gastric juice and in intestinal juice below pH 7, but soluble in colonic intestinal juice, whereby the dosage form releases the 5-amino-salicylic acid, salt or ester to the right side of the colon.

10. The composition as claimed in claim 9 wherein the layer is 60 to 150 microns thick.

11. The composition as claimed in claim 10 wherein said layer contains said anionic copolymer as the only coating polymer.

12. The composition as claimed in claim 9 wherein the layer is 95 to 135 microns thick.

13. The composition as claimed in claim 12 wherein said layer contains said anionic copolymer as the only coating polymer.

14. The composition as claimed in claim 9 wherein the layer is 120 microns thick.

15. The composition as claimed in claim 14 wherein said layer contains said anionic copolymer as the only coating polymer.

16. The composition as claimed in claim 9 wherein the said oral dosage form is a capsule or tablet.

17. The composition as claimed in claim 9 wherein said individual particles are not coated.

18. A method of treating ulcerative colitis or Crohn's disease of the colon comprising orally administering to a person suffering therefrom the composition of claim 9 whereby the 5-amino-salicylic acid is released to the right side of the colon.

19. An orally administrable pharmaceutical composition for selectively administering 5-amino-salicylic acid, or pharmaceutically acceptable salt or ester thereof, to the large intestine, comprising a solid oral dosage form containing a pharmaceutically effective amount for the treatment of ulcerative colitis or Crohn's disease of the colon of said 5-amino-salicylic acid, salt or ester, said solid oral dosage form being coated with a layer of composition containing an anionic copolymer of methacrylic acid and methacrylic acid methyl ester, in which the ratio of free carboxyl groups to ester groups is about 1:2, and which layer is insoluble in gastric juice and in intestinal juice below pH 7, but soluble in colonic intestinal juice, whereby the dosage form releases the 5-amino-salicylic acid, salt or ester to the right side of the colon.

* * * * *

UNITED STATES PATENT AND TRADEMARK OFFICE
CERTIFICATE OF CORRECTION

PATENT NO. : 5,541,171  
DATED : July 30, 1996  
INVENTOR(S) : JOHN RHODES, et al.

Page 1 of 2

It is certified that error appears in the above-indentified patent and that said Letters Patent is hereby corrected as shown below:

On the Title Page, under item [62], change "which is a continuation of PCT/00235, Jul. 28, 1982" to --, all abandoned--, and between items [62] and [30], insert the following:

--[86] PCT No.: PCT/GB82/00235  
     371 Date: Mar. 30, 1983  
     102(e) Date: Mar. 30, 1983  
[87] PCT Pub. No. WO83/00435  
     PCT Pub. Date: Feb. 17, 1983--

Col. 1, lines 9 and 10, delete "which is a continuation of PCT/GB82/00235, Jul. 28, 1982" and insert --, all abandoned.--

Claim 1 (column 10 line 33), after "acid", insert --in a therapeutic amount--.

UNITED STATES PATENT AND TRADEMARK OFFICE
CERTIFICATE OF CORRECTION

PATENT NO. : 5,541,171
DATED : July 30, 1996
INVENTOR(S) : JOHN RHODES, et al.

It is certified that error appears in the above-indentified patent and that said Letters Patent is hereby corrected as shown below:

On the title page, the disclaimer notice should refer to --5,541,170-- instead of to "5,541,171".

Signed and Sealed this

Fourth Day of February, 1997

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO.   : 5,541,171
DATED        : July 30, 1996
INVENTOR(S)  : JOHN RHODES, et al.

It is certified that error appears in the above-indentified patent and that said Letters Patent is hereby corrected as shown below:

Claim 4 (column 10, line 39), change "Claim 3" to --Claim 2--.

Change the number of Claim 6 at column 10, lines 43-44, to --5--.

Change the number of Claim 5 at column 10, lines 41-42, to --6--.

Column 10, line 41, change "1" to --5--.

Signed and Sealed this

Eleventh Day of March, 1997

Attest:

BRUCE LEHMAN

Attesting Officer    Commissioner of Patents and Trademarks